United States Patent [19] [11] 4,228,173
Cairns et al. [45] Oct. 14, 1980

[54] THIOPYRANO-BENZOPYRANS, COMPOSITIONS AND METHOD OF USE THEREOF

[75] Inventors: Hugh Cairns; Anthony H. Ingall, both of Loughborough, England

[73] Assignee: Fisons Limited, London, England

[21] Appl. No.: 58,609

[22] Filed: Jul. 18, 1979

[30] Foreign Application Priority Data

Aug. 15, 1978 [GB] United Kingdom ............... 33433/78

[51] Int. Cl.² ..................... A61K 31/28; C07D 497/04
[52] U.S. Cl. .................................... 424/269; 424/275; 549/27; 548/252; 548/253
[58] Field of Search .................. 549/27; 548/252, 253; 424/269, 275

[56] References Cited

U.S. PATENT DOCUMENTS 3,804,857  4/1974  Cairns et al. .......................... 549/27
3,952,013  4/1976  Hazard et al. ......................... 549/27

FOREIGN PATENT DOCUMENTS 2721021  11/1977  Fed. Rep. of Germany ........... 548/253

Primary Examiner—Henry R. Jiles
Assistant Examiner—Robert T. Bond

Attorney, Agent, or Firm—Merriam, Marshall & Bicknell

[57] ABSTRACT

There are described compounds of formula I,

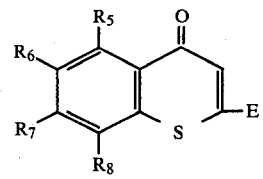

in which an adjacent pair of $R_5$, $R_6$, $R_7$ and $R_8$ form a chain —COCH═CE—O—, and the remainder of $R_5$, $R_6$, $R_7$ and $R_8$, which may be the same or different, each represent hydrogen, hydroxy, alkyl, halogen, alkenyl, alkoxy, or —$NR_1R_2$ in which $R_1$ and $R_2$, which are the same or different, are each hydrogen or alkyl, and E is —COOH, a 5-tetrazolyl group or an (N-tetrazol-5-yl) carboxamido group, and pharmaceutically acceptable derivatives thereof.

There are also described processes for making the compounds and pharmaceutical, e.g. anti-allergic, compositions containing them.

9 Claims, No Drawings

THIOPYRANO-BENZOPYRANS, COMPOSITIONS AND METHOD OF USE THEREOF

This invention relates to new sulphur containing compounds, compositions containing them and methods for their preparation.

According to our invention we provide compounds of formula I,

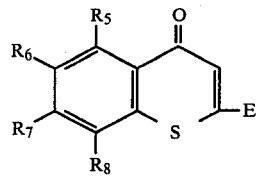

in which an adjacent pair of $R_5$, $R_6$, $R_7$ and $R_8$ form a chain —COCH=CE—O—, and the remainder of $R_5$, $R_6$, $R_7$ and $R_8$, which may be the same or different, each represent hydrogen, hydroxy, alkyl, halogen, alkenyl, alkoxy, or —$NR_1R_2$ in which $R_1$ and $R_2$, which are the same or different, are each hydrogen or alkyl, and E is —COOH, a 5-tetrazolyl group or an (N-tetrazol-5-yl) carboxamido group, and pharmaceutically acceptable derivatives thereof.

According to our invention we also provide a process for the production of a compound of formula I or a pharmaceutically acceptable derivative thereof, which comprises, (a) producing a compound of formula I in which E is —COOH by selectively hydrolysing or oxidising a compound of formula II,

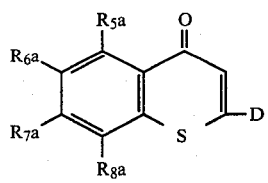

in which $R_{5a}$, $R_{6a}$, $R_{7a}$ and $R_{8a}$ have the same significances as $R_5$, $R_6$, $R_7$ and $R_8$ above, save that an adjacent pair of $R_{5a}$, $R_{6a}$, $R_{7a}$ and $R_{8a}$ may represent a chain of formula —COCH=C($D_1$)O—, and one or both of D and $D_1$ represents a group hydrolysable or oxidisable to a —COOH group, and the other may represent a —COOH group, (b) producing a compound of formula I in which E is —COOH, or an ester thereof, by cyclising a compound of formula III,

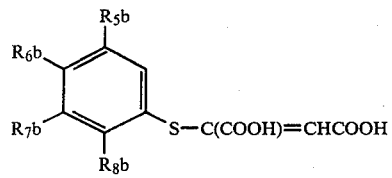

or an ester thereof, in which $R_{5b}$, $R_{6b}$, $R_{7b}$ and $R_{8b}$ have the same significances as $R_5$, $R_6$, $R_7$ and $R_8$ above, save that an adjacent pair of $R_{5b}$, $R_{6b}$, $R_{7b}$ and $R_{8b}$ may represent the pair of groups —H and —O—C(COOH)=CH—COOH, or an ester thereof, (c) producing a compound of formula I in which E is —COOH by cyclising a compound of formula V,

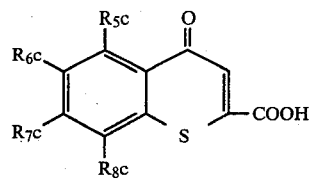

or an ester thereof, in which $R_{5c}$, $R_{6c}$, $R_{7c}$ and $R_{8c}$ have the same significances as $R_5$, $R_6$, $R_7$ and $R_8$ above save that an adjacent pair of $R_{5c}$, $R_{6c}$, $R_{7c}$ and $R_{8c}$, instead of forming a chain —COOH=C(COOH)—O—, represent the pair of groups:

(i) —COCH$_2$CO—COR″ and —OM or a halogen atom, or (ii) —H and —O—C(COR″)=CH—COR″

R″ represents —OM, or a group which is hydrolysable thereto, and

M represents hydrogen or an alkali metal, and if necessary or desired hydrolysing the group —COR″, to a group —COOM, (d) producing a compound of formula I in which E is a 5-tetrazolyl group by reacting a corresponding compound of formula I in which E is —CN, with an azide in a solvent which is inert under the reaction conditions, or (e) producing a compound of formula I in which E is an (N-tetrazol-5-yl)carboxamido group by reacting a corresponding compound of formula I in which E is —COOH, or an acid halide, ester or mixed anhydride thereof, with 5-aminotetrazole, and if necessary or desired hydrolysing the ester of the compound of formula I and/or converting the compound of formula I to a pharmaceutically acceptable derivative thereof.

In process (a) the group D may be, for example an ester, acid halide, amide or a nitrile group, which may be hydrolysed to a —COOH group. The hydrolysis may be carried out using conventional techniques, for example under mildly basic conditions, e.g. using sodium carbonate, sodium hydroxide, sodium bicarbonate, or under acidic conditions, e.g. a mixture of aqueous dioxan and hydrochloric acid, or hydrogen bromide in acetic acid. The hydrolysis may be carried out at a temperature of from about 25° to 120° C. depending on the compounds used. Alternatively the group D may be an alkyl, e.g. a lower alkyl such as methyl, a hydroxymethyl, an aralkenyl, e.g. styryl, an acyl, e.g. a lower alkanoyl such as acetyl, or a formyl group. The oxidation may be carried out using conventional techniques which do not otherwise modify the molecule to such an extent that the yield of the desired product is uneconomical, for example an alkyl or a hydroxymethyl group may be oxidised using selenium dioxide, e.g. under reflux in aqueous dioxan; or chromic acid, e.g. under reflux in aqueous acetic acid. Aralkenyl groups may be oxidised using, for example neutral or alkaline potassium permanganate in aqueous ethanol, and acyl groups may be oxidised using, for example chromic acid or an aqueous hypochlorite, e.g. sodium hypochlorite. The formyl group may be oxidised using, for example chromic acid or silver oxide.

In process (b) the cyclisation may be carried out by treating the compound of formula III with a cyclising agent, for example a dehydrating agent such as chlorosulphonic, sulphuric or polyphosphoric acid. The reaction is preferably carried out under anhydrous conditions and may be carried out at a temperature of from about 25° to 150°, and preferably from 75° to 150° C. Compounds of formula III may also be cyclised by subjecting the compound to an elevated temperature, e.g. of from 200° to 250° C., optionally in the presence of a high boiling solvent which is inert under the reaction conditions, e.g. diphenyl ether.

When one of the groups is —OM the cyclisation of process (c)(i) may be carried out by heating, or under basic or neutral conditions. It is however preferred to carry out the cyclisation in the presence of an acid, e.g. hydrochloric acid, and in a solvent which is inert under the reaction conditions, e.g. ethanol. The reaction may be carried out at from about 20° to 150° C. The group —COR" is preferably an ester group, e.g. R" may be a lower alkoxy group. When one of the groups is halogen the cyclisation may be carried out in a solvent which is inert under the reaction conditions, preferably a high boiling polar solvent, e.g. pyridine, dimethylformamide or hexamethylphosphoramide. The reaction is preferably carried out with the aid of a strong base, for example an alkali metal hydride, e.g. sodium hydride. The reaction is preferably carried out at a temperature of from about 80° to 200° C., in the absence of free oxygen, e.g. under an inert atmosphere such as nitrogen.

The cyclisation of process (c)(ii) may be carried out by treating the compound of formula V with a cyclising agent, for example a dehydrating agent such as chlorosulphonic, polyphosphoric or sulphuric acid. The reaction is preferably carried out under anhydrous conditions and may be carried out at a temperature of from 0° to 100° C. Alternatively cyclisation may be achieved by converting the free carboxy groups of the compound of formula V to acyl halide groups and subjecting the resulting acyl halide to an intramolecular Friedel-Crafts reaction.

Suitable solvents which are inert under the reaction conditions of process (d) include those in which both the reagents are soluble, e.g. N,N-dimethylformamide. Other solvents which may be mentioned include dimethylsulphoxide, tetrahydrofuran, diethyl glycol and ethyl methyl glycol. The reaction is preferably carried out at a temperature of from about 20° to 130° C. for from about 1 to 20 hours. The azide used in the reaction is preferably ammonium or an alkali metal azide, e.g. sodium or lithium azide, but other azides, e.g. aluminium azide or the azides of nitrogen containing bases, e.g. mono-, di-, tri-, and tetra- methyl-ammonium, anilinium, morpholinium and piperidinium azides, may also be used if desired. Where an azide other than that of an alkali metal is used this azide may be prepared in the reaction mixture by double decomposition. The reaction may, if desired, be carried out in the presence of an electron acceptor, e.g. aluminium chloride, boron trifluoride, ethyl sulphonic acid or benzene sulphonic acid. As an alternative to the reaction conditions set out above, the reaction may be carried out using hydrazoic acid (hydrogen azide) at a temperature of from about 20° to 150° C. in a suitable solvent, under greater than atmospheric pressure. When an azide other than hydrazoic acid is used, e.g. sodium azide, the product of the reaction will be the corresponding tetrazole salt. This salt may readily be converted to the free acid by treatment with strong acid, e.g. hydrochloric acid.

In process (e) the anhydride is preferably a mixed anhydride of such a type that it will cleave preferentially, to give the desired chromone carboxamidotetrazole as the major product when reacted with the 5-aminotetrazole. Examples of suitable acids from which the mixed anhydride may be derived are sulphonic acids e.g. benzene sulphonic acid, sterically hindered carboxylic acids, e.g. pivalic, isovaleric, diethylacetic or triphenylacetic acid, and alkoxy formic acids, e.g. a lower alkoxy formic acid such as ethoxy or isobutoxy formic acid. When an acid halide is used it may conveniently be an acid chloride. The reaction is preferably carried out under anhydrous conditions in a solvent which will not react with either the 5-aminotetrazole or the mixed anhydride or acid halide, e.g. pyridine or dimethylformamide. However when the reaction is carried out in a non-basic solvent, e.g. dimethylformamide, an adequate proportion of an acid acceptor, e.g. triethylamine, should also preferably be present. The reaction is preferably carried out at a temperature of from about −15° to +20° C. When an ester is used we prefer to use a nitrophenyl ester, e.g. a p-nitrophenyl ester and to carry out the reaction in a solvent which is inert under the reaction conditions, e.g. dimethylformamide, at a temperature of from about 100° to 150° C. When a compound of formula I in which E is —COOH is used as starting material the reaction may be carried out by heating the compound of formula I and the 5-aminotetrazole in a solvent which is inert under the reaction conditions, e.g. dimethylacetamide, at a temperature of from 100° to 200° C. Alternatively the reaction may be carried out in the presence of a condensation agent, e.g. N,N'-carbonyldiimidazole or dicyclohexyl carbodiimide, in an aprotic solvent, e.g. dimethylformamide, at a temperature of from about 10° to 40° C.

The starting materials for processes (b) and (c) may be made from known compounds in one or more steps using processes known per se.

The compounds of formula II may be made as described above or by a process analogous to process (c) (i).

Alternatively the compounds of formula II may, for example in the case of the acid halide, the amide and the nitrile, be made from compounds of formula I using conventional techniques, e.g. reaction of an ester of the compound of formula I with ammonia to produce the amide, followed by dehydration of the amide to form the nitrile.

The compounds of formula I in which E is —CN may be made by dehydrating the corresponding amide using, for example, phosphorus oxychloride, as dehydrating agent. The reaction is preferably carried out using at least one molar equivalent of dehydrating agent per mole of the amide. Where the dehydrating agent reacts with one of $R_5$, $R_6$, $R_7$ or $R_8$ (e.g. a substituent comprising an —OH group) sufficient dehydrating agent should be used to satisfy the side reaction as well as the main reaction. The reaction may, if desired, be carried out in the presence of an acid binding agent, e.g. triethylamine. The reaction may be carried out in the presence of a solvent, e.g. N,N-dimethylformamide, dimethyl sulphoxide, pyridine, benzene or hexamethyl phosphoramide, or an excess of the dehydrating agent may be used as the reaction medium. The reaction may be carried out at a temperature of from about 0° to 200° C.

depending on the dehydrating agent used. When phosphorus oxychloride is used a temperature of from 0° to 100° C. is preferred.

The amide starting materials may be made by reacting a corresponding ester with ammonia, using techniques conventional in the production of amides from esters, e.g. using an alkanol as solvent at a temperature of 0° to 120° C.

The processes as described above may produce the compound of formula I or a derivative thereof. It is also within the scope of this invention to treat any derivative so produced to liberate the free compound of formula I, or to convert one derivative into another.

The compounds of formula I and the intermediates therefor may be isolated from their reaction mixtures using conventional techniques.

Pharmaceutically acceptable derivatives of the compounds of formula I include pharmaceutically acceptable salts, and when E is a —COOH group, esters and amides of the 2-carboxylic acid group. Suitable salts include ammonium, alkali metal (e.g. sodium, potassium and lithium) and alkaline earth metal (e.g. calcium or magnesium) salts, and salts with suitable organic bases, e.g. salts with hydroxylamine, lower alkylamines such as methylamine or ethylamine, with substituted lower alkylamines, e.g. hydroxy substituted alkylamines such as tris(hydroxymethyl)methylamine, or with simple monocyclic nitrogen heterocyclic compounds, e.g. piperidine or morpholine. Suitable esters include simple lower alkyl esters, e.g. the ethyl ester, esters derived from alcohols containing basic groups, e.g. di-lower alkyl amino substituted alkanols such as the β(diethylamino)-ethyl ester, and acyloxy alkyl esters, e.g. a lower acyloxy-lower alkyl ester such as the pivaloyloxymethyl ester, or a bis-ester derived from a di-hydroxy compound, e.g. a di(hydroxy-lower alkyl) ether, e.g. the bis-2-oxapropan-1,3-diyl ester. The pharmaceutically acceptable acid addition salts of the basic esters, and also of those compounds in which one of $R_5$, $R_6$, $R_7$ and $R_8$ is a group —$NR_1R_2$, e.g. the hydrochloride, the hydrobromide, the oxalate, the maleate or the fumarate salts, may also be used. The esters may be made by conventional techniques, e.g. esterification or transesterification. The amides may be, for example, unsubstituted or mono- or di- C 1 to 6 alkyl amides and may be made by conventional techniques, e.g. reaction of an ester of the corresponding acid with ammonia or an appropriate amine.

The compounds of formula I and pharmaceutically acceptable derivatives thereof are useful because they possess pharmacological activity in animals; in particular they are useful because they inhibit the release and/or action of pharmacological mediators which result from the in vivo combination of certain types of antibody and specific antigen, e.g. the combination of reaginic antibody with specific antigen (see Example 27 of British patent specification No. 1,292,601). The new compounds have also been found to interfere with reflex pathways in experimental animals and man, and in particular those reflexes associated with lung function. In man, both subjective and objective changes which result from the inhalation of specific antigen by sensitised subjects are inhibited by prior administration of the new compounds. Thus the new compounds are indicated for use in the treatment of reversible airway obstruction and/or to prevent the secretion of excess mucous. The new compounds are thus indicated for the treatment of allergic asthma, so-called 'intrinsic' asthma (in which no sensitivity to extrinsic antigen can be demonstrated), bronchitis, coughs and the nasal and bronchial obstructions associated with the common cold. The new compounds may also be of value in the treatment of other conditions in which antigen-antibody reactions or excess mucous secretion are responsible for, or are an adjunct to, disease, for example, hay fever; certain eye conditions, e.g. trachoma; alimentary allergy, e.g. urticaria and atopic eczema; and gastrointestinal conditions, for example gastrointestinal allergy, especially in children, e.g. milk allergy, or ulcerative colitis.

For the above mentioned uses the dosage administered will, of course, vary with the compound employed, the mode of administration and the treatment desired. However, in general, satisfactory results are obtained when the compounds are administered at a dosage of from 0.001 to 50 mg per kg of animal body weight in the test set out in Example 27 of British patent specification No. 1,292,601. For man the indicated total daily dosage is in the range of from 0.01 mg to 1,000 mg preferably from 0.01 mg to 200 mg and more preferably from 1 mg to 60 mg, which may be administered in divided doses from 1 to 6 times a day or in sustained release form. Thus unit dosage forms suitable for administration (by inhalation or oesophageally) comprise from 0.01 mg to 50 mg, preferably 0.01 mg to 20 mg and more preferably from 0.01 mg to 10 mg of the compound preferably admixed with a solid or liquid pharmaceutically acceptable diluent, carrier or adjuvant.

The compounds of formula I, and pharmaceutically acceptable derivatives thereof, have the advantage that they are more efficacious in certain pharmacological models, (e.g. the ability to block the hypotensive effect of sodium cromoglycate in the dog) or are longer acting or are less toxic than compounds of similar structure to the compounds of formula I. Furthermore the compounds of formula I, and pharmaceutically acceptable derivatives thereof, are advantageous in that they are more efficaceous in interfering with reflex pathways and in inhibiting the secretion of mucous than are compounds of similar structure to the compounds of formula I.

We prefer each of $R_1$, $R_2$, $R_5$, $R_6$, $R_7$ and $R_8$, when they contain carbon, to contain up to 8, and preferably up to 4 carbon atoms. Specifically we prefer $R_5$, $R_6$, $R_7$ and $R_8$ to be selected from hydrogen, methoxy, propyl, allyl, methyl, ethyl, chlorine, bromine, mono- or di-methylamino, and hydroxy. $R_1$ and $R_2$ may be, for example, methyl, ethyl or n-butyl. The —COCH=CE—O— chain may be bonded to the benzene ring in any sense and in any of the adjacent positions $R_5$, $R_6$, $R_7$, $R_8$. However, we prefer the chain to be bonded in the positions $R_6$ and $R_7$ the —O— part of the chain being in position $R_7$ or in the positions $R_5$ and $R_6$ the —O— part of the chain being in the position $R_6$. We also prefer the group E to be a —COOH group.

According to the invention there is also provided a process for the production of a pharmaceutically acceptable salt of a compound of formula I, which comprises treating a compound of formula Ic,

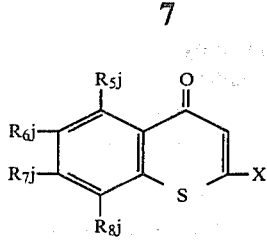

in which $R_{5j}$, $R_{6j}$, $R_{7j}$ and $R_{8j}$ have the same significances as $R_5$, $R_6$, $R_7$ and $R_8$ above, save that an adjacent pair of $R_{5j}$, $R_{6j}$, $R_{7j}$ and $R_{8j}$ may form a chain —O—C(X)=CHCO—, and X is a 5-tetrazolyl group, an (N-tetrazol-5-yl)carboxamido group, a carboxylic acid group (or an ester thereof, or another salt thereof), a nitrile group, an acid halide group or an amide group, with a compound containing an available pharmaceutically acceptable cation and capable of converting the group X to a pharmaceutically acceptable salt of an E group.

Compounds capable of converting the group X to a pharmaceutically acceptable salt of an E group include compounds, e.g. bases and ion exchange resins, containing pharmaceutically acceptable cations, e.g. sodium, potassium, calcium, ammonium and appropriate nitrogen containing organic cations. In general we prefer to form the pharmaceutically acceptable salt by treating the free acid of formula I with an appropriate base, e.g. with an alkaline-earth or alkali metal hydroxide, carbonate or bicarbonate in aqueous solution or by a metathetical process with an appropriate salt. When a strongly basic compound is used care should be taken, e.g. by keeping the temperature sufficiently low, to ensure that the compound of formula I is not hydrolysed or otherwise degraded. The pharmaceutically acceptable salt may be recovered from the reaction mixture by, for example, solvent precipitation and/or removal of the solvent by evaporation, e.g. by freeze drying.

According to our invention we also provide a pharmaceutical composition comprising (preferably less than 80%, and more preferably less than 50% by weight) of a compound of formula I, or a pharmaceutically acceptable derivative thereof, in combination with a pharmaceutically acceptable adjuvant, diluent or carrier. Examples of suitable adjuvants, diluents or carriers are: for tablets capsules and dragees; microcrystalline cellulose, calcium phosphate, diatomaceous earth, a sugar such as lactose, dextrose or mannitol, talc, stearic acid, starch, sodium bicarbonate and/or gelatin; for suppositories, natural or hardened oils or waxes; and for inhalation compositions, coarse lactose. The compound of formula I, or the pharmaceutically acceptable derivative thereof, preferably is in a form having a mass median diameter of from 0.01 to 10 microns. The compositions may also contain suitable preserving, stabilising and wetting agents, solubilizers, sweetening and colouring agents and flavourings. The compositions may, if desired, be formulated in sustained release form. We prefer compositions which are designed to be taken oesophageally and to release their contents in the gastrointestinal tract.

The 5-tetrazolyl and (N-tetrazol-5-yl)carboxamido groups are of formulae XVII and XVIII respectively,

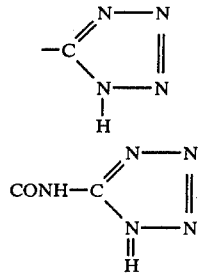

The invention is illustrated, but in no way limited by the following Examples.

EXAMPLE 1

4,5-Dioxo-4H,5H,thiopyrano[3,2-f]benzopyran-2,7-dicarboxylic acid (a) Ethyl 6-hydroxy-4-oxo-4H-1-benzothiopyran-2-carboxylate 6-Hydroxy-4-oxo-4H-1-benzothiopyran-2-carboxylic acid (20 g) was heated in ethanol (500 ml) at reflux overnight with a few drops of concentrated sulphuric acid as catalyst. The solution was evaporated to small volume and flooded with water. The resulting solid was filtered off, washed with saturated sodium bicarbonate solution, water and dried. The product was recrystalised from ethanol as a yellow solid (13.7 g) 61%. m.p. 216°–217°.

(b) 2-(2-Carboxy-4-oxo-4H-1-benzothiopyranyl-6-oxy)but-2-ene-1,4-dioic acid

Ethyl 6-hydroxy-4-oxo-4H-1-benzothiopyran-2-carboxylate (10 g), dimethyl acetylene dicarboxylate (5.7 g) and 'Triton B' (10 drops) were heated at reflux in ethanol (200 ml) overnight. The solution was evaporated to dryness and the resulting green oil chromatographed on a silica column using chloroform as eluant. The fractions containing the major product were collected and evaporated to give an oil (12.0 g).

The oil was heated with sodium bicarbonate (7.2 g), water (200 ml) and ethanol (50 ml) at reflux for 4 hours. The mixture was cooled, acidified with concentrated hydrochloric acid and extracted with ethyl acetate. The ethyl acetate extracts were washed with water, dried over MgSO₄, filtered and evaporated to dryness. The residue was triturated with ether and the resulting solid filtered off and dried (5.6 g), 42%. Characterised by NMR spectrum which showed that the trans isomer predominated.

(c) 4,5-Dioxo-4H,5H-thiopyrano[3,2-f]benzopyran-2,7-dicarboxylic acid 2-(2-Carboxy-4-oxo-4H-1-benzothiopyranyl-6-oxy)-but-2-ene-1,4-dioic acid (5.6 g) was added to chlorosulphonic acid (25 ml) cooled to 0°. The mixture was then heated at 60° for 90 minutes. The solution was cooled and poured cautiously onto crushed ice and the resulting solid filtered off and recrystallised from dimethylsulphoxide to give a pale green solid. The solid was dissolved in saturated sodium bicarbonate solution and the solution acidified with dilute hydrochloric acid solution. The solid was filtered off and dried (1.8 g) 34%. mp. 280°. Characterised by NMR.

(d) Disodium 4,5-dioxo-4H,5H-thiopyrano[3,2-f]benzopyran-2,7-dicarboxylate 4,5-Dioxo-4H,5H-thiopyrano[3,2-f]benzopyran-2,7-dicarboxylic acid (1.49 g) and sodium bicarbonate (0.788 g) were dissolved in water (25 ml) and the solution filtered and cooled to 0° C. The resulting white solid was filtered off and dried in vacuo 0.8 g, 49%.

calculated for $C_{14}H_4Na_2O_7S + 14.9\%$ $H_2O$ C=39.5 H=2.6: found C=39.4 H=2.5.

EXAMPLE 2

Disodium 4,6-dioxo-10-propyl-4H,6H-thiopyrano[3,2-g]-1-benzopyran-2,8-dicarboxylate

(a) O-(4-Acetyl-3-hydroxy-2-propylphenyl)-N,N-dimethylthiocarbamate 2,4-Dihydro-3-propylacetophenone (5 g) potassium carbonate (4.3 g) and N,N-dimethylthiocarbamoyl chloride (4.1 g) were stirred in dry acetone (100 mls) for 3 hours at room temperature and then refluxed overnight. The whole was poured into water and the precipitated solid collected by filtration and dried to give 7.0 g of product, NMR and MS evidence was consistent for the required product.

(b) S-(4-Acetyl-3-hydroxy-2-propylphenyl)-N,N-dimethylthiocarbamate

The product of step (a) (1 g) was added to diphenyl ether (20 mls) which was at reflux. The reaction mixture was refluxed for a further 5 minutes after addition, cooled and the diphenyl ether removed by distillation under reduced pressure. The residue was treated with 40°–60° petroleum ether cooled in a solid $CO_2$ and the solid product was collected by filtration and dried to give 0.7 g of the desired product—NMR and MS evidence were consistent for the required product.

(c) 2-Hydroxy-4-mercapto-3-propylacetophenone

The product of step (b) (0.7 g) and 10% aqueous sodium hydroxide (5 mls) were refluxed in methanol (20 mls) under nitrogen for 5 hours. The reaction mixture was cooled, poured into 10% hydrochloric acid and extracted with ether. The extracts were washed with water, dried and the solvent evaporated to give 0.5 g of product. NMR and MS were consistent for the required product.

(d) 2-(4-Acetyl-3-hydroxy-2-propylphenylthio)but-2-ene-1,4-dioic acid

The product of step (c) (51.8 g) was treated with potassium hydroxide (48.3 g) in water (300 mls) and shaken until complete dissolution had occurred. Acetylene dicarboxylic acid monopotassium salt (41.3 g) suspended in water (200 mls) was added to the above solution and the reaction mixture heated on the steambath for 30 minutes with occasional shaking. The whole was cooled in ice, acidified with concentrated hydrochloric acid, and the resultant precipitate extracted with ether, washed with water and dried. The solvent was evaporated, and the residue triturated with 40°–60° petroleum ether, collected by filtration and dried to give 51.4 g of the desired product.

Structure was confirmed by NMR and MS evidence.

(e) 6-Acetyl-7-hydroxy-4-oxo-8-propyl-4H-1-benzothiopyran-2-carboxylic acid The product of step (d) (2 g) was heated with polyphosphoric acid (15 mls) for 30 minutes. The reaction mixture was poured into ice/water and extracted with ethyl acetate, which was then washed with water and dried. The solvent was evaporated and the residue triturated with ether, collected by filtration and dried to give 0.3 g of product. A recrystallisation from ethyl acetate gave material mp 245°–246° C.

Analysis: Found: C; 58.4%, H; 4.67%, S; 10.3%: $C_{15}H_{14}O_5S$ Required: C; 58.8%, H; 4.6%, S; 10.5%.

(f) Ethyl 6-Acetyl-7-hydroxy-4-oxo-8-propyl-4H-1-benzothiopyran-2-carboxylate The product of step (e) (10 g) was refluxed for 24 hours in ethanol (350 mls) which had previously been saturated with hydrogen chloride gas. The reaction mixture was poured into water, extracted with ether, which was washed with sodium bicarbonate solution then water and dried. The solvent was evaporated to leave 7.5 g of residual product. Structure was confirmed by NMR and MS.

(g) Diethyl 4,6-dioxo-10-propyl-4H,6H-thiopyrano[3,2-g]-1-benzopyran-2,8-dicarboxylate The product of step (f) (7.5 g) and diethyl oxalate (24.4 mls) in dry dimethylformamide (200 mls) were added to ether washed 50% sodium hydride (4.3 g) in dry dimethylformamide (250 mls) with stirring under nitrogen. The whole was stirred for a further 24 hours after addition, then poured into ice/water and extracted into ethyl acetate which was dried, filtered and the solvent evaporated to afford a red solid. This was added to ethanol (100 mls) previously saturated with hydrogen chloride gas and refluxed for 15 minutes. The reaction mixture was poured into water, extracted with chloroform, dried and the solvent evaporated to give 4.9 g of the desired product. Structure confirmed by MS and NMR.

(h) 4,6-Dioxo-10-propyl-4H,6H-thiopyrano[3,2-g]-1-benzopyran-2,8-dicarboxylic acid The product of step (g) (2.7 g) in glacial acetic acid (100 mls) and 48% aqueous hydrobromic acid (6 mls) was heated under reflux for 4 hours. More aqueous hydrobromic acid (3 mls) was added and refluxing continued overnight. The reaction was allowed to cool and the precipitated solid was collected by filtration, washed with ether and dried in vacuo at 80° C. for 3 hours to give 2.0 g of the desired product, mp 308°–310° dec.

Analysis: Found: C; 56.1%, H; 3.4%, S; 8.9%: $C_{17}H_{12}O_7S$ Required: C; 56.7%, H; 3.3%, S; 8.9%.

(i) Disodium 4,6-dioxo-10-propyl-4H,6H-thiopyrano[3,2-g]-1-benzopyran-2,8-dicarboxylate The product of step (h) (1.935 g) and sodium bicarbonate (0.903 g) in distilled water (50 mls) were shaken until complete dissolution had occurred. The solution was filtered and the filtrate freeze dried to give 2.2 g of the desired product.

Analysis: Found: C; 46.3%, H; 3.25%: $C_{17}H_{10}Na_2O_7S$ Required: C; 46.3%, H; 3.21%, 8.3% water.

We claim:

1. A compound of formula I,

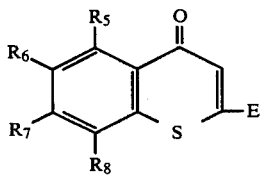

in which an adjacent pair of $R_5$, $R_6$, $R_7$ and $R_8$ form a chain —COCH=CE—O—, and the remainder of $R_5$, $R_6$, $R_7$ and $R_8$, which may be the same or different, each represent hydrogen, hydroxy, alkyl, halogen, alkenyl, alkoxy, or —$NR_1R_2$ in which $R_1$ and $R_2$, which are the same or different, are each hydrogen or alkyl, each of $R_1$, $R_2$, $R_5$, $R_6$, $R_7$ and $R_8$, when they contain carbon, containing up to 8 carbon atoms, and E is —COOH, a 5-tetrazolyl group or an (N-tetrazol-5-yl) carboxamido group, and pharmaceutically acceptable salts, esters and amides thereof.

2. A compound according to claim 1, wherein each of $R_1$, $R_2$, $R_5$, $R_6$, $R_7$ and $R_8$, when they contain carbon, contain up to 4 carbon atoms.

3. A compound according to claim 1, wherein $R_5$, $R_6$, $R_7$ and $R_8$ are selected from hydrogen, methoxy, propyl, allyl, methyl, ethyl, chlorine, bromine, mono- or di-methylamino, and hydroxy.

4. A compound according to claim 1, wherein the —COCH=CE—O— chain is bonded in the positions $R_6$ and $R_7$, or in the positions $R_5$ and $R_6$.

5. A compound according to claim 1, wherein E is —COOH.

6. A compound according to claim 1 in the form of a pharmaceutically acceptable salt thereof.

7. A compound according to claim 1, which is selected from 4,5-Dioxo-4H,5H-thiopyrano[3,2-f]benzopyran-2,7-dicarboxylic acid, 4,6-dioxo-10-propyl-4H,6H-thiopyrano[3,2-g]-1-benzopyran-2,8-dicarboxylic acid and pharmaceutically acceptable salts of either thereof.

8. A pharmaceutical composition suitable for the treatment of reversible airway obstruction or to prevent secretion of excess mucous comprising an effective amount of a compound according to claim 1 in combination with a pharmaceutically acceptable adjuvant, diluent or carrier.

9. A method for the treatment of reversible airway obstruction or for the prevention of the excretion of excess mucous which comprises administration of an effective amount of a compound according to claim 1 to a patient suffering from such a condition.

* * * * *